(12) United States Patent
Bliss et al.

(10) Patent No.: US 9,187,724 B1
(45) Date of Patent: Nov. 17, 2015

(54) METHOD TO OPTIMIZE THE UTILIZATION OF CAPTURED CARBON DIOXIDE THROUGH THE CULTIVATION AND PROCESSING OF MICROALGAE

(71) Applicants: Charles Bliss, Springfield, VA (US); Mason Charles Moseley, Fairfax, VA (US)

(72) Inventors: Charles Bliss, Springfield, VA (US); Mason Charles Moseley, Fairfax, VA (US)

(*) Notice: Subject to any disclaimer, the term of this patent is extended or adjusted under 35 U.S.C. 154(b) by 0 days.

(21) Appl. No.: 14/261,854

(22) Filed: Apr. 25, 2014

(51) Int. Cl.
C12N 1/12 (2006.01)
C12M 1/00 (2006.01)
C12P 3/00 (2006.01)
C12P 1/00 (2006.01)

(52) U.S. Cl.
CPC ............. *C12M 29/24* (2013.01); *C12M 21/02* (2013.01); *C12M 43/08* (2013.01); *C12P 1/00* (2013.01); *C12P 3/00* (2013.01)

(58) Field of Classification Search
None
See application file for complete search history.

(56) References Cited

U.S. PATENT DOCUMENTS

| | | | |
|---|---|---|---|
| 6,492,149 B1 | 12/2002 | Muller-Feuga | |
| 2008/0178739 A1 | 7/2008 | Lewnard et al. | |
| 2008/0190024 A1 | 8/2008 | Hobbs | |
| 2009/0049748 A1 | 2/2009 | Day et al. | |
| 2009/0151241 A1 | 6/2009 | Dressler et al. | |
| 2009/0294354 A1 | 12/2009 | Theodore et al. | |
| 2009/0305388 A1 | 12/2009 | Dressler et al. | |
| 2010/0011778 A1 | 1/2010 | Knight et al. | |
| 2010/0190227 A1 | 7/2010 | Dauth et al. | |
| 2010/0285576 A1 | 11/2010 | Norbeck et al. | |
| 2010/0297739 A1 | 11/2010 | Steiner et al. | |
| 2010/0304452 A1 | 12/2010 | Oyler | |
| 2011/0003357 A1 | 1/2011 | Barclay et al. | |
| 2011/0287507 A1 | 11/2011 | Martin et al. | |

OTHER PUBLICATIONS

Xiao, Manual making of a parabolic solar collector, Jan. 4, 2009, Available online at: wims.unice.fr/xiao/solar/diy-en.pdf.*
Mazloumi et al., Simulation of solar lithium bromide—water absorption cooling system with parabolic trough collector, Energy Conversion and Management, vol. 49, Issue 10, Oct. 2008, pp. 2820-2832.*

* cited by examiner

*Primary Examiner* — Karen Cochrane Carlson
*Assistant Examiner* — Jennifer M. H. Tichy
(74) *Attorney, Agent, or Firm* — Howard M. Cohn; Daniel Cohn

(57) ABSTRACT

A method for cultivating and processing microalgae includes directing a continuous supply of carbon dioxide into an enclosed photobioreactor containing microalgae. The enclosed photobioreactor is exposed to insolation for the cultivation of the microalgae by means of controlled photosynthesis chemical reactions. The microalgae are cultivated and the microalgae are processed to create an algae biomass and a gaseous mixture. The algae biomass is extracted to produce an essentially pure algae oil and oil free algae biomass. The gaseous mixture is separated into unreacted carbon dioxide and oxygen. The separated unreacted carbon dioxide is recycled to the photobioreactor and the oxygen in excess of export quantity is stored.

28 Claims, 8 Drawing Sheets

METHOD TO OPTIMIZE THE UTILIZATION OF CAPTURED CARBON DIOXIDE THROUGH THE CULTIVATION AND PROCESSING OF MICROALGAE

TECHNICAL FIELD OF THE INVENTION

The present invention relates generally to optimizing the utilization of captured carbon dioxide from fossil-energy installations by the cultivation of microalgae in a closed system subjected to solar radiation (insolation) with consequent processing to commercially-attractive algae oil, biomass residue, and essentially pure oxygen gas. Particularly, the present invention relates to matching a 24/7 supply of captured carbon dioxide with inherently periodic and variable availability of solar radiation (insolation) during daylight hours. Further, the present invention relates to export of the products from processing the microalgae (algae oil and essentially pure oxygen) at rates that markets require despite their variable production rates. Markets for algae oil are likely to exist for its use as a fuel oil and in its further processing to biodiesel fuel. Markets for pure oxygen already exist.

BACKGROUND OF THE INVENTION

The worldwide industrial revolution of the past two centuries changed the energy scene from essentially total global reliance on renewable energy to global reliance practically entirely on fossil energy forms, with the consequence of elevated carbon dioxide content in the atmosphere with its potential for deleterious climate change. Consequently, worldwide concern exists toward developing means to protect the atmosphere by capturing carbon dioxide produced from fossil-fuel combustion in order to avoid its emission to the atmosphere. Two technologically-feasible options exist for avoiding emission to the atmosphere. One option lies in storage of captured carbon dioxide under high-pressure in underground geological formations and accepting the costs without compensating revenues. The other option lies in the use of captured carbon dioxide for enhancing the production of petroleum crude oil through its injection under high pressure into mature oil fields with the receipt of compensating revenues. These two options generally are referred to as sequestration of captured carbon dioxide.

The photosynthesis process by which microalgae can be cultivated from captured carbon dioxide involves a series of complex chemical reactions in which carbon dioxide, water, nutrients, and insolation are converted to an oil-rich algae biomass and essentially pure oxygen gas. Through recycling, the carbon dioxide is completely consumed.

Considerable intensive worldwide research and development activity currently exists aimed at two modes of algae cultivation: one in open ponds and the other in enclosed structures known as photobioreactors. The open-pond mode can be characterized as requiring large land areas in terms of their output, as subject to adverse impact in the form of invasion by unwanted algae species, as impacted by the effects of wind, evaporation, storms, and as losses of some of the carbon dioxide to the atmosphere. Moreover, the oxygen produced by the photosynthesis reactions is not recoverable. Because of these disadvantages, the use of photobioreactors is a preferred means of using carbon dioxide.

Current world-wide research and development work in algae cultivation is largely based on the use of a diluted form of carbon dioxide in combustion gases from fossil energy power generating installations and its direct transport to algae cultivation installations. Emerging development in fossil-energy based power generating systems such as oxyfuel combustion promises by-product streams of virtually 100% content (neat) carbon dioxide as contrasted with the about 13-15 volume % conventional carbon-dioxide content in chimney gases. Chemical reaction rates in the photosynthesis process, like all chemical reactions, increase markedly when there is an excess of a key reactant, which the neat carbon dioxide can facilitate.

Given surpluses in the reactants, carbon dioxide and water, reaction rates will be determined by the availability of photons from insolation.

SUMMARY OF THE INVENTION

The present invention enables photobioreactors to optimize the chemical reactions involved in photosynthesis through maximized production of algae biomass and subsequent processing for maximized collection of the gaseous oxygen product, for processing the algae biomass for maximum extraction of its oil content, and for isolation of the essentially oil-free biomass residue.

The present invention provides for on-site production of its peak electricity demand and for minimizing its consumption of water beyond the fixed requirement for water to support the chemical reactions in the photosynthesis process.

The present invention provides for internal illumination within each photobioreactor tube with photon wavelengths that are readily absorbed in the photosynthesis process so that algae production, which requires insolation, can be continuously available.

The present invention anticipates that the oxygen produced from photosynthesis will include appreciable amounts of unreacted carbon dioxide which must be removed and reused for photosynthesis so that the oxygen can be marketable. Accordingly, the present invention provides a processing component in the system for removal of such carbon dioxide content and its ultimate recycle to the photobioreactors.

The present invention anticipates that purified oxygen will be marketed on a 24/7 constant flow rate basis, while it will be produced at variable flow rates depending on the daily, seasonal, and yearly pattern of insolation at the site of the installations. To assure marketability for the oxygen, this invention provides facilities for the liquefaction and storage of the oxygen produced in excess of the marketing rate and facilities for the evaporation of stored oxygen to make up for oxygen production rates below the marketing rate.

The present invention anticipates that carbon dioxide captured from fossil-energy consuming installations will be delivered as a constant rate on a 24/7 basis, while the ability of the photobioreactors to absorb carbon dioxide will vary throughout the day in accordance with insolation. Accordingly, the present invention provides for the receipt of captured carbon dioxide and liquefying and storing excess quantities during nighttime hours and delivering the excess stored during the daytime hours, as required.

The present invention provides for oxygen liquefaction to achieve the necessary minimized enthalpy level by the use of a refrigerant. The present invention uses a portion of the liquefied carbon dioxide as the refrigerant to help supply the required enthalpy minimization.

The present invention provides for a photovoltaic electricity-producing field adjacent to the area occupied by the photobioreactors, which then operates in synchronism with the pattern of peak demand from the electrical consumption of compressors used in the liquefaction processes for carbon dioxide and oxygen.

The present invention anticipates the need to minimize, if not eliminate, makeup water consumption and provides facilities for this purpose so that the system can be installed in areas that are either desert or semi-arid, where supplies of fresh water are either limited or non-existent. The system requires process water to support the photosynthesis process in the photobioreactors and requires makeup water in the component of the system that supplies cooling water to the photobioreactors and to the liquefaction equipment.

According to the present invention, a method for cultivating and processing microalgae, comprises directing a continuous supply of carbon dioxide into an enclosed photobioreactor containing microalgae; exposing the enclosed photobioreactor to insolation for the cultivation of the microalgae by means of controlled photosynthesis chemical reactions; cultivating the microalgae and processing the microalgae to create an algae biomass and a gaseous mixture; separating the algae biomass from the gaseous mixture; separating the algae biomass into essentially pure algae oil and oil free algae biomass; separating the gaseous mixture into unreacted carbon dioxide and oxygen; recycling the separated unreacted carbon dioxide to the photobioreactor; and storing the oxygen.

Further according to the present invention, a system for cultivating and processing microalgae, comprises means for directing a continuous supply of carbon dioxide into an enclosed photobioreactor containing microalgae; means for exposing the enclosed photobioreactor to insolation for the cultivation of the microalgae by means of controlled photosynthesis chemical reactions; means for cultivating the microalgae and processing the microalgae to create an algae biomass and a gaseous mixture; means for separating the algae biomass from the gaseous mixture; means for separating the algae biomass into essentially pure algae oil and oil free algae biomass; means for separating the gaseous mixture into unreacted carbon dioxide and oxygen; recycling the separated unreacted carbon dioxide to the photobioreactor; and means for storing the oxygen.

BRIEF DESCRIPTION OF THE DRAWINGS

The structure, operation, and advantages of the present invention will become further apparent upon consideration of the following description taken in conjunction with the accompanying figures (Figs.). The figures are intended to be illustrative, not limiting. Certain elements in some of the figures may be omitted, or illustrated not-to-scale, for illustrative clarity. The cross-sectional views may be in the form of "slices", or "near-sighted" cross-sectional views, omitting certain background lines which would otherwise be visible in a "true" cross-sectional view, for illustrative clarity.

In the drawings accompanying the description that follows, both reference numerals and legends (labels, text descriptions) may be used to identify elements. If legends are provided, they are intended merely as an aid to the reader, and should not in any way be interpreted as limiting.

DETAILED DESCRIPTION OF THE PREFERRED EMBODIMENTS

The present invention is generally directed to the linkage between an Algae Cultivation and Processing system and a constant 24/7 supply of carbon dioxide.

Figure 1:
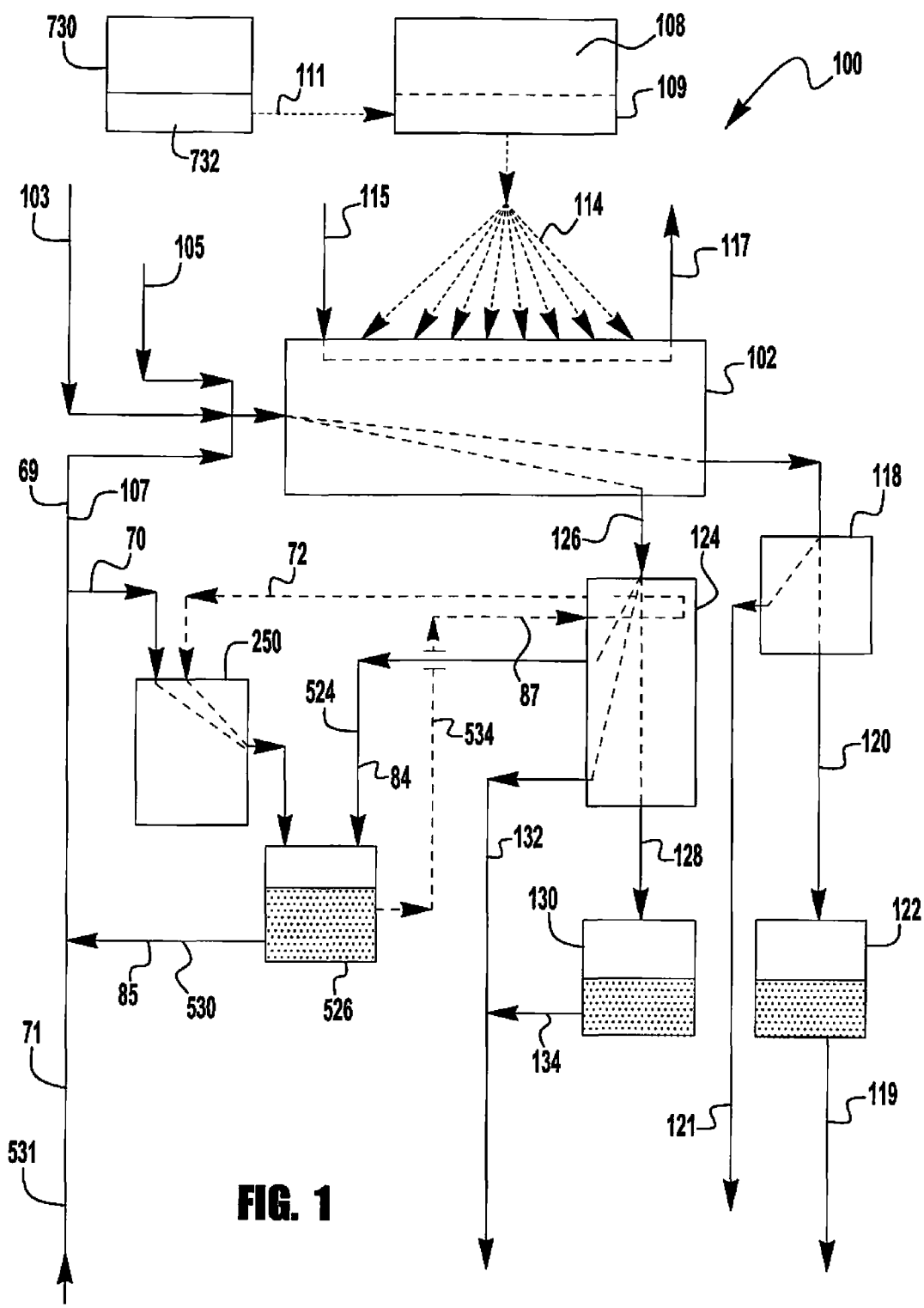
FIG. 1 is a schematic view of a system for receiving carbon dioxide at a constant rate, cultivating microalgae and processing microalgae for the extraction of its oil, for the isolation of by-product oxygen, for the recycling of unreacted carbon dioxide, and for the processing of oil-free algae bio-mass, in accordance with the present invention.

FIG. 1 is a schematic view of the algae cultivation and processing system 100, in accordance with the present invention, in which captured carbon dioxide, process water, and nutrients, are directed to a photobioreactor 102 containing microalgae. The carbon dioxide demand, as established by the daily pattern of insolation in the photobioreactors 102, is supplied in the quantity 69 through a line 107. The quantity is determined from the constant 24/7 supply 71 through line 531 by either withdrawal of a portion 70 or the addition of a portion 85 through line 530. The process water is sent through a line 103 to the photobioreactor 102. The nutrients are sent through a line 105 to the photobioreactor 102. Within photobioreactor 102 complex chemical reactions occur in which carbon dioxide, water, nutrients, and insolation convert the microalgae to an oil-rich algae biomass and a gaseous mixture. Further the system 100 is used to separate the algae biomass into essentially pure algae oil and oil free algae biomass. The system 100 is also used to separate the gaseous mixture into unreacted carbon dioxide and oxygen.

FIG. 1 also shows a source of insolation 108 and an internal source of illumination 109. As discussed hereinafter, Parallel rays 114 are directed to the photobioreactor 102. Electricity 111 can be provided either from an external source or generated within the system 100 as discussed hereinafter. A stream of cooling water can be directed into and out of photobioreactor 102 through lines 115 and 117, respectively.

Figure 2:
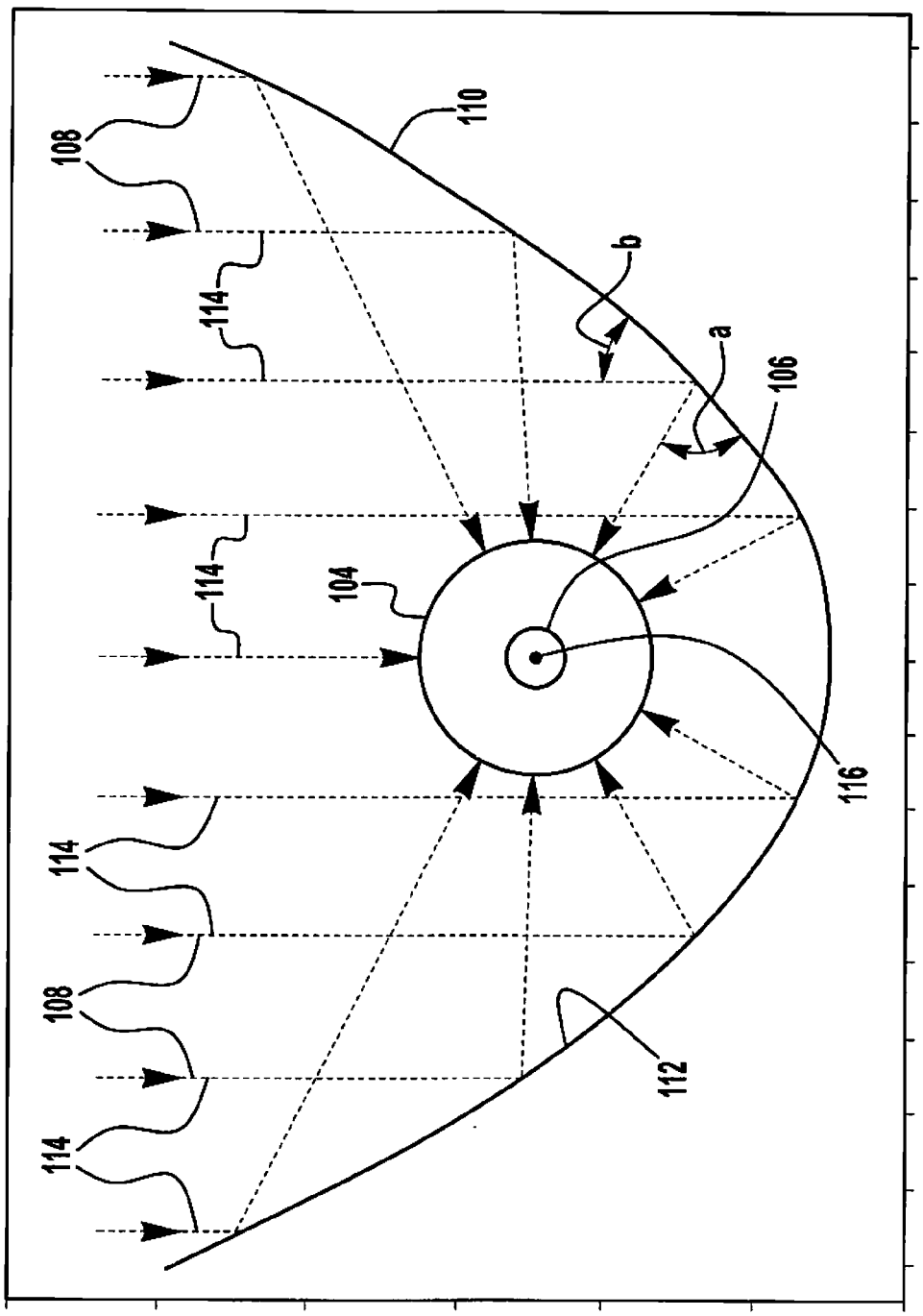
FIG. 2 illustrates a reflecting parabolic insolation accumulator to maximize the flow of photons into photobioreactor tubes, in accordance with the present invention.
Figure 3:
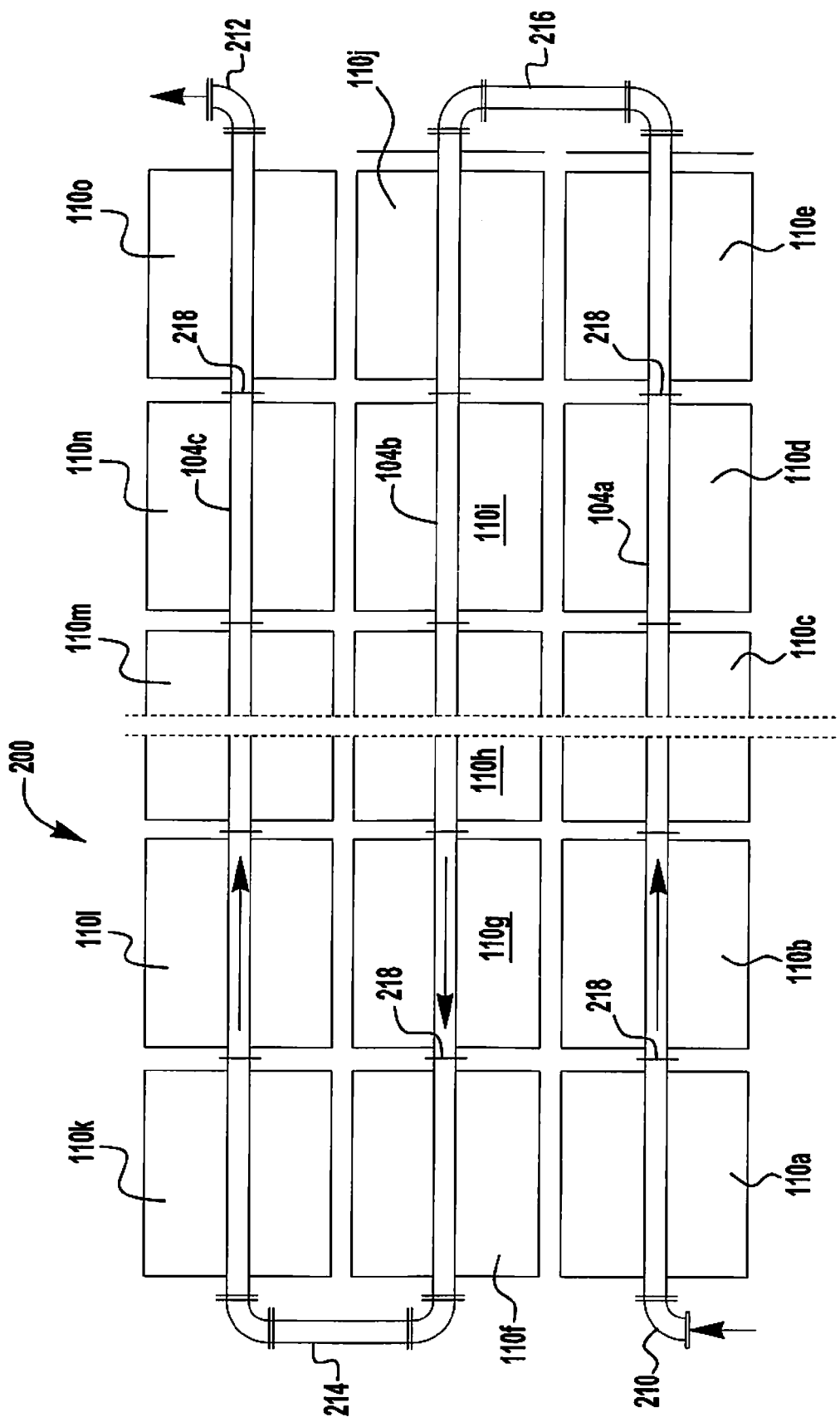
FIG. 3 is a plan view of the general arrangement of a photobioreactor array, in accordance with the present invention.

The algae cultivation and processing system 100 comprises an array of photobioreactors 102, as shown in FIG. 2 and FIG. 3, which each consist of interconnected horizontal tubes 104, preferably circular tubes, containing concentric inner circular tubes 106 (FIG. 2), which are internally electrically illuminated by a suitable means that produces radiation in the desired wavelengths. Each array of circular inner tubes 104 provides sufficient length of travel to provide adequate residence time during the flow period for the chemical reactions involved in the photosynthesis process to complete to the desired stage. The number of arrays of inner tubes 104 is selected for parallel flow to provide the processing capacity needed to accommodate the maximum quantity of carbon dioxide delivered to the photobioreactors 102.

In FIG. 2, the photobioreactor arrays receive insolation 108 of varying intensities during daylight hours and at levels depending on the geographic location of the algae cultivation and processing system. Because the chemical reactions in the photobioreactors for the photosynthesis process to proceed toward completion are already provided with reactants far in excess of the stoichiometric requirements, the rate of reactions will in turn be limited by the rates at which the photons in the insolation 108 penetrate the photobioreactor circular tubes 104.

FIG. 2 illustrates the means to maximize the flow of photons 108 into the photobioreactor circular tubes 104. A reflecting parabolic structure 110 having a reflecting parabolic surface 112 in which the photobioreactor circular tube 104 is located such that the center of the tube is exactly at the focal point 116 of the parabolic surface 112. Because of the extreme distance of the sun from the Earth, the insolation 108 arrives as parallel 'rays" 114. These "rays" 114 act in accordance with the principle that the angle "a" of reflection of a ray from a surface is equal to the angle of incidence "b" of the ray on the surface. Note that the equality, while not evident from the drawing, is based on measuring the angle from the tangent line (not shown) at the point where the ray strikes the surface of the parabola. Since the reflecting surface 112 has the mathematical properties of a parabola, all reflected rays aim toward the focal point 116 of the parabola, in effect concentrating the received photons within the photobioreactor tubes 104. FIG. 2 illustrates this principle. The wavelengths of the internal illumination within the photobioreactor tubes 104, which are optimum for enhancing algae cultivation, concentrate at the low end and high end of the visible spectrum.

FIG. 2 illustrates the location of a concentric, smaller-diameter tube 106 within the photobioreactor tube 104. A length of light-emitting elements (not shown) of wavelengths favored by the photosynthesis process are mounted within the concentric tube 106 of circular tube 104 such that radiation of the photons occurs over a 360° range. The purpose of this artificial radiation is twofold. The primary purpose is to maintain a level of algae cultivation during the nighttime hours that avoids the phenomenon of cessation of the chemical reactions in photosynthesis, thereby avoiding a delay in restoring these reactions when daylight hours begin. The secondary purpose is to maintain a level of algae cultivation near the center of the photobioreactor tube 104, where photons from insolation cannot generally penetrate because of the distance from the outer surface of the photobioreactor tube 104.

FIG. 3 illustrates the general arrangement of a photobioreactor array 200 of a plurality of interconnected photobioreactor tubes 104a, 104b and 104c disposed within a plurality of reflecting parabolic insolation accumulators 110a, 110b, 110c, 110d, 110e, 110f, 110g, 110h, 110i, 110j, 110k, 110l, 110m, 110n, 110o (110a-110o) in plan view. The concentric inner tubes 106, having a length of light-emitting elements therein, within the photobioreactor tubes 104 are shown in (see FIG. 2). The parabolic reflector surfaces for each of the reflecting parabolic insolation accumulators 110a-110o are disposed beneath the photobioreactor tubes 104a, 104b and 104c to reflect the parallel 'rays" 114 of the insolation 108 toward the focal point of the parabolic reflector surfaces 112 (see FIG. 2). Thus, the received photons are concentrated within the photobioreactor tubes 104. The photobioreactor tubes 104 may be oriented in a north-south direction and the vertical axis of the parabolic reflecting accumulators (110a-110o) rotated in synchronization with the movement of the sun in the sky from dawn until sunset In order to maximize the receipt of photons.

The reflecting parabolic insolation accumulators 110a-110o are constructed in spaced relationship to each other to allow for the use of supporting structures (not shown) to hold the reflecting parabolic insolation accumulators 110a-110o in the desired positions and for drainage of rainwater that might accumulate on the parabolic reflector surfaces 112.

Fittings 210 and 212 at the ends of tubes 104a and 104c, respectively, allow for return flow. One or more tubular heat exchangers 214 are inserted at periodic intervals in the interconnected tubes 104, such as between tubes 104b and 104c and tubes 104a and 104b, respectively, to cool the reactants and products flowing through the interconnected tubes 104 to maintain an optimum temperature range for the cultivation of algae. The parabolic structure 110a-110o, illustrated in FIG. 3, will concentrate insolation with infrared wavelengths, which can heat the contents of the photobioreactor tubes 104 excessively. One or more mixing devices 218, such as a disc and donut configuration, is disposed at periodic intervals in interconnected tubes 104 to homogenize the reactants and products and thereby facilitate the exposure of unreacted materials to the photons. Periodically a means of structural support 218 for the photobioreactor tubes 104 is installed.

In FIG. 1, an algae oil extraction device 118 extracts the combustible oil content of the algae biomass and delivers the combustible oil content through a line 120 to a storage container 122 and then through a line 119 from which it can be marketed at appropriate rates. The oil free algae biomass from the oil extraction device 118 is disposed of through line 121.

In FIG. 1, component 124 is a means for the separating unreacted carbon dioxide from the oxygen in the gaseous mixture received through line 126 from the photobioreactor 102. Component 124 is a means for the liquefaction of the oxygen in the gaseous mixture received from the photobioreactor 102. The liquefied oxygen is then directed through a line 132 for marketing purposes and the excess to a storage container 130 and through a line 128. As required, liquid oxygen can be directed from storage container 130 through a line 134 to the extent that marketing at a uniform rate requires.

Figure 4:
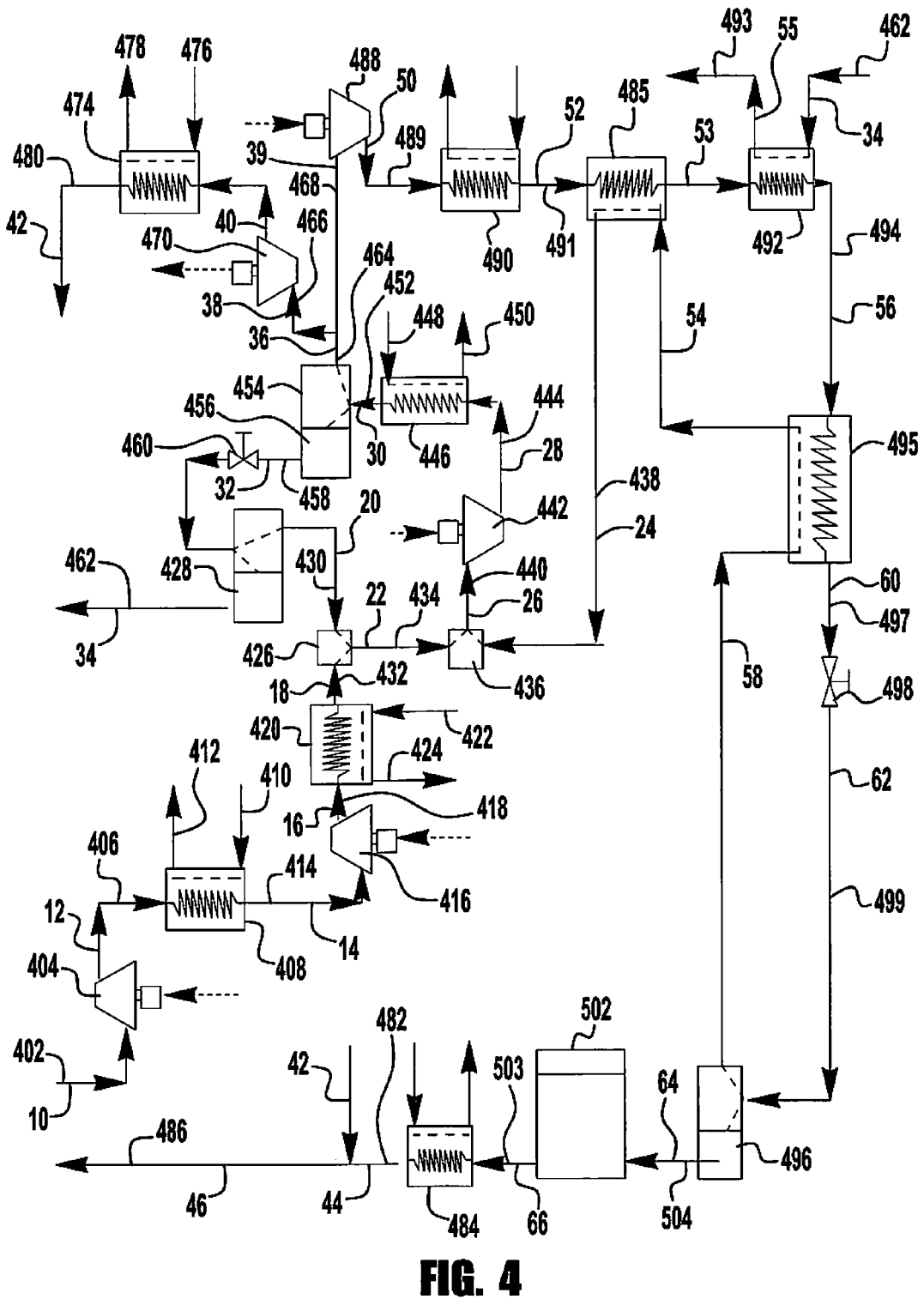
FIG. 4 is a schematic diagram that illustrates a separation and liquefaction process, in accordance with the present invention.

FIG. 4 is a schematic diagram that illustrates the separation and oxygen liquefaction process of component 124 shown in FIG. 1. FIG. 4 shows the flow of streams for processing the gaseous mixture from the photobioreactor to produce liquefied carbon dioxide and liquefied oxygen.

A principle for the processing scheme is raising the pressure of the incoming gaseous mixture stream 10, being delivered from the photobioreactor 102 through line 402 to a level where the carbon dioxide content condenses at ambient temperature, leaving essentially carbon dioxide-free oxygen to proceed toward liquefaction. Another principle is avoiding unnecessary oxygen liquefaction, if the intention is that gaseous oxygen is to be marketed through a pipeline that accepts oxygen at a constant 24/7 rate. However, the oxygen is produced from the photosynthesis reactions at variable rates and at maximum levels during the daytime hours and at almost insignificant levels during the nighttime hours. Surplus production is then liquefied for inventory and extraction when needed.

The pressure of stream 10 is increased to an intermediate level in a compressor 404 with an accompanying increase in its temperature to create a stream 12 delivered through a line 406 to a cooler 408 having a cooling water stream flowing in and out through lines 410 and 412, respectively. The temperature of stream 12 is lowered by cooler 408 by heat exchange with the cooling water stream. Stream 14 exiting cooler 408 through line 414 has its pressure and temperature further increased in compressor 416. Stream 16 exiting compressor 416 through a line 418 passes through cooler 420 wherein its temperature is decreased to about ambient conditions by a cooling water stream flowing in and out of cooler 420 through lines 422 and 424, respectively.

In mixer 426, a stream 20 directed from flash drum 428 through line 430 is joined with stream 18 flowing through line 432 to the mixer 426. Stream 20 exiting mixer 426 through line 430 is carbon dioxide vapor that is produced when the carbon dioxide content in stream 22 is eventually extracted, as described below. The resulting stream 22 flowing through line 434 between mixer 426 and mixer 436 is then mixed with stream 24 flowing through line 438 into mixer 436 to form stream 26 flowing through line 440 to compressor 442. Stream 26 includes oxygen vapor that is eventually produced when the oxygen is liquefied, as described further below.

The pressure of stream 26 is then increased in the compressor 442. The temperature of the resulting stream 28 flowing through line 444 to a cooler-condenser 446 is then reduced by a cooling water stream flowing in and out through lines 448 and 450, respectively, of the cooler-condenser 446. The resulting stream 30 flows through line 452 to flash drum 454, in which under the prevailing temperature and pressure conditions the oxygen content of the gases flashes to a vapor and the carbon dioxide content of stream 20 settles in the flash drum as a liquid. The combination of temperature and pressure in stream 30 represents saturation such that, with sufficient heat exchange in the cooler condenser 446, condensation of the carbon dioxide to a liquid occurs.

Accordingly, the flash drum 454 receives stream 30 and allows separation of the liquid carbon dioxide from the oxygen vapor. Since the pressure in the flash drum 454 is considerably higher than the pressure at which liquid carbon dioxide is stored, the pressure of the liquid carbon dioxide 456 flowing out of the flash drum 454 through line 458 as stream 32 is reduced at constant enthalpy (Joule-Thompson expansion) thereby producing the stream of liquid carbon dioxide and carbon dioxide vapor after flow through an expansion valve 460 from line 458. The vapor/liquid mix is separated in the flash drum 428. The stream 34 of liquid carbon dioxide produced in flash drum 428 is sent through a line 462 to a storage container (not shown). The stream 20 of carbon dioxide vapor is sent through line 430 to mixer 426 as noted above.

Stream 36 flowing from flash drum 454 through line 464 is now essentially oxygen vapor. Stream 36 is split as required with stream 38 through line 466 representing oxygen that can be immediately exported and stream 39 flowing through line 468 representing oxygen vapor to be subjected to liquefaction.

Since the pressure level in oxygen stream 38 is substantially higher than the pressure at which the oxygen is to be exported by pipeline, stream 38 is directed through line 466 to an expander 470. The pressure is reduced in the expander as required and electricity is generated. The temperature of the stream 38 is also significantly reduced to form oxygen stream 40 in line 472. The temperature of stream 40 is increased in water cooler 474 through heat exchange with a water stream flowing in and out through lines 476 and 478, respectively. Stream 42 exiting water cooler 474 through line 480 is then suited for joining the exit stream 44 of oxygen flowing through line 482 from a water cooler 484 for export through line 486 as stream 46.

The pressure of the stream 39 of oxygen flowing through line 468, which resulted from the split of stream 36, is raised in compressor 488 to the desired level as stream 50 flowing through line 489, which then is cooled by a cooling water stream flowing in and out of cooler 490, which produces stream 52 in line 491. The cooled stream 52 is further cooled to stream 53 by heat exchange in cooler 485 with oxygen vapor from stream 54, which then as stream 24 is sent to mixer 436 as has been described hereinbefore. Stream 53 is further cooled by heat exchange in cooler 492 through evaporation of liquid carbon dioxide refrigerant in stream 34 and 55 flowing through lines 462 and 493, respectively. The cooled oxygen stream then exits cooler 492 in line 494 as stream 56.

Final cooling occurs for stream 56 in cooler 495 through heat exchange with oxygen vapor stream 58 from the flash drum 496 to produce a stream 60 of oxygen vapor in line 497. The objective for all of the cooling steps is to reduce the enthalpy in stream 60 to a minimum before it is subjected to expansion under constant enthalpy (Joule-Thomson expansion) by passing it through an expansion valve 498 for attaining temperature at which a maximum of the stream liquefies as oxygen stream 62 flowing through line 499. It is also within the terms of the embodiment that the expansion valve 498 may be replaced with an expansion turbine (not shown) whereby the cooled oxygen flowing through the turbine liquefies with simultaneous production of electricity.

The flash drum 496 separates the liquid oxygen from stream 62 and delivers it to a storage container 502 through line 504 as stream 64. The oxygen vapor from the flash drum 496 as stream 58 represents a recycle of extremely low-temperature, unliquified oxygen, which through its use in heat-exchange cooling as described above, is eventually blended as stream 24 with stream 22 in mixer 436.

Liquid oxygen, assuring a constant 24/7 export through a pipeline, is withdrawn from storage container 502 through line 503 as stream 66, and evaporated in water cooler 484. It then exits water cooler 484 in line 482 as stream 44, combined with stream 42, which as stream 46 is exported through line 486 at a constant 24/7 rate.

Figure 5:
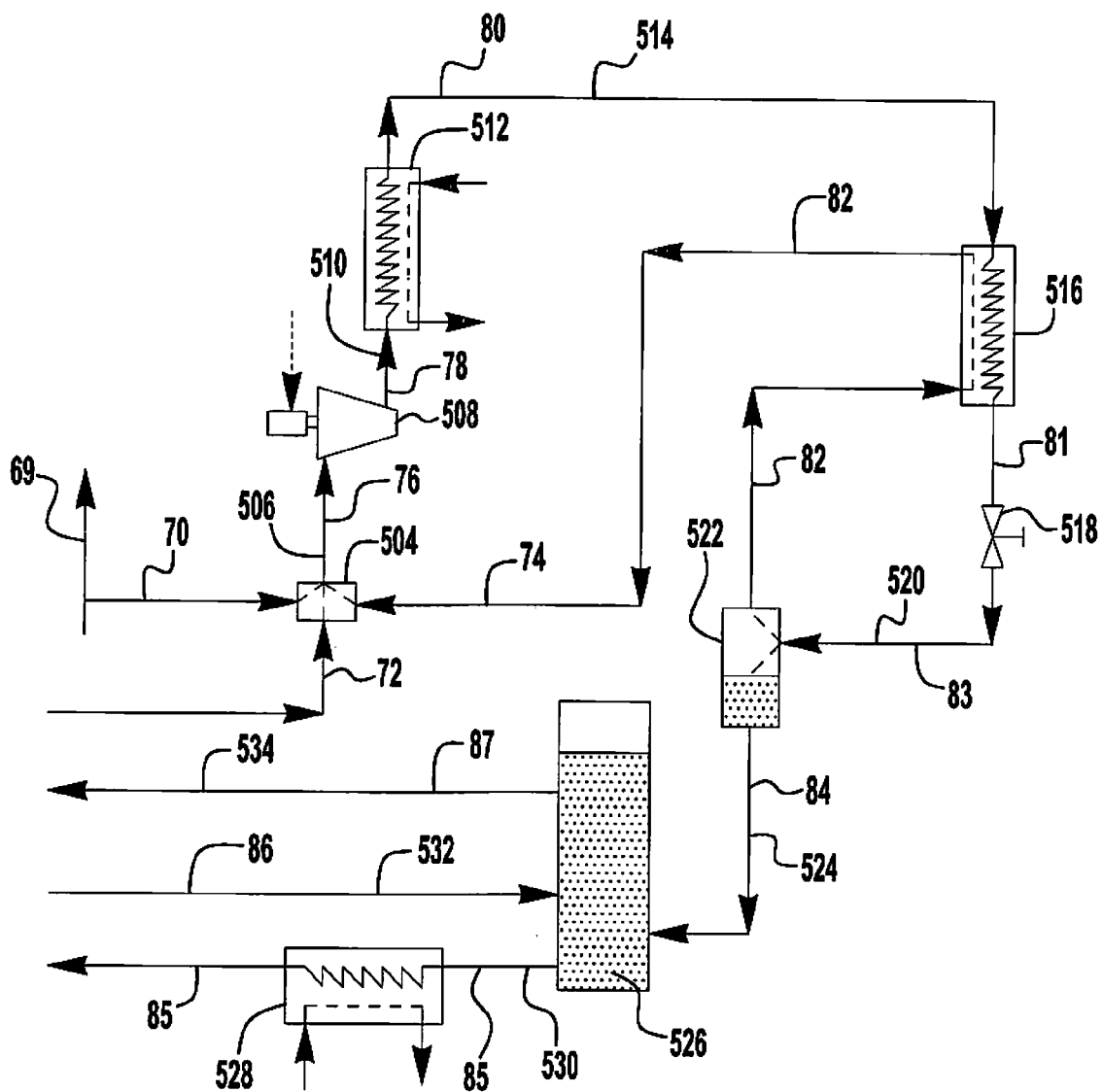
FIG. 5 is a schematic diagram that illustrates a method for placing unneeded carbon dioxide in inventory and releasing it when needed, in accordance with the present invention.

In FIG. 1, the carbon dioxide liquefaction system 250 is an illustrative means for matching a constant 24/7 receipt of captured carbon dioxide with the variable demand for carbon dioxide in the photobioreactors 102. FIG. 5 is a schematic diagram that illustrates the flow of streams, received at a constant level on a 24/7 basis, for processing the carbon dioxide by the liquefaction component 250.

Referring to FIG. 5, carbon dioxide vapor is received in the carbon dioxide liquefaction component 250 from two sources: stream 70 represents receipt, especially during the night time hours, of carbon dioxide that cannot be accepted completely by the photobioreactors because of lack of solar radiation. This is indicated in FIG. 1 also as stream 70. Stream 72 represents receipt of carbon dioxide vapor from the use of carbon dioxide liquid as a refrigerant for the liquefaction of oxygen. This is indicated in FIG. 1 also as stream 72.

The mixer 504 blends both streams 70 and 72 with stream 74, which is a recycle stream for the vapor residual from the ultimate liquefaction of the carbon dioxide as noted below. The pressure level in the blended streams forming the resulting stream 76 in line 506 is raised in the compressor 508. Stream 78, which emerges from compressor 508 through line 510, is also at an elevated temperature and is cooled in the cooler 512 to ambient conditions. The stream 80 of carbon dioxide exits the cooler 512 through line 514. At the pressure and temperature of stream 80, the carbon dioxide exists as a liquid.

Stream 80 is further directed through line 514 to cooler 516, is cooled in the cooler 516, and exits as stream 81 through heat exchange with stream 82, which stream as noted above is a recycle stream for the vapor residual from the ultimate liquefaction of the carbon dioxide. The cooled stream 82, as Stream 74, becomes the recycle stream for mixer 504 as noted above.

The pressure in stream 81 is reduced at constant enthalpy (Joule-Thomson expansion) through flow in the expansion valve 518. The mixture of liquid and vapor thus produced as stream 83 flows through line 520 and is separated in the flash drum 522 with the vapor stream 82 becoming the recycle stream noted above and the liquid stream 84 delivered through line 524 to storage container 526.

The daytime requirement for carbon dioxide is withdrawn from the storage container 526 as stream 85 to evaporator 528 through line 530 and then as stream 85 through line 528 becomes the makeup for the daytime carbon dioxide demand (FIG. 1). The stream 86 of liquid carbon dioxide separated from the photobioreactor off gases (FIG. 4) is delivered to storage container 526 through line 532 from the component 124 (FIG. 1) for separating carbon dioxide from the oxygen in the off gases delivered through line 126 from the photobioreactors 102 (FIG. 1).

A stream 87 of liquid carbon dioxide is withdrawn from storage container 526 through line 534 as the refrigerant in the processing to liquefy oxygen in component 124 (FIG. 1).

Figure 6:
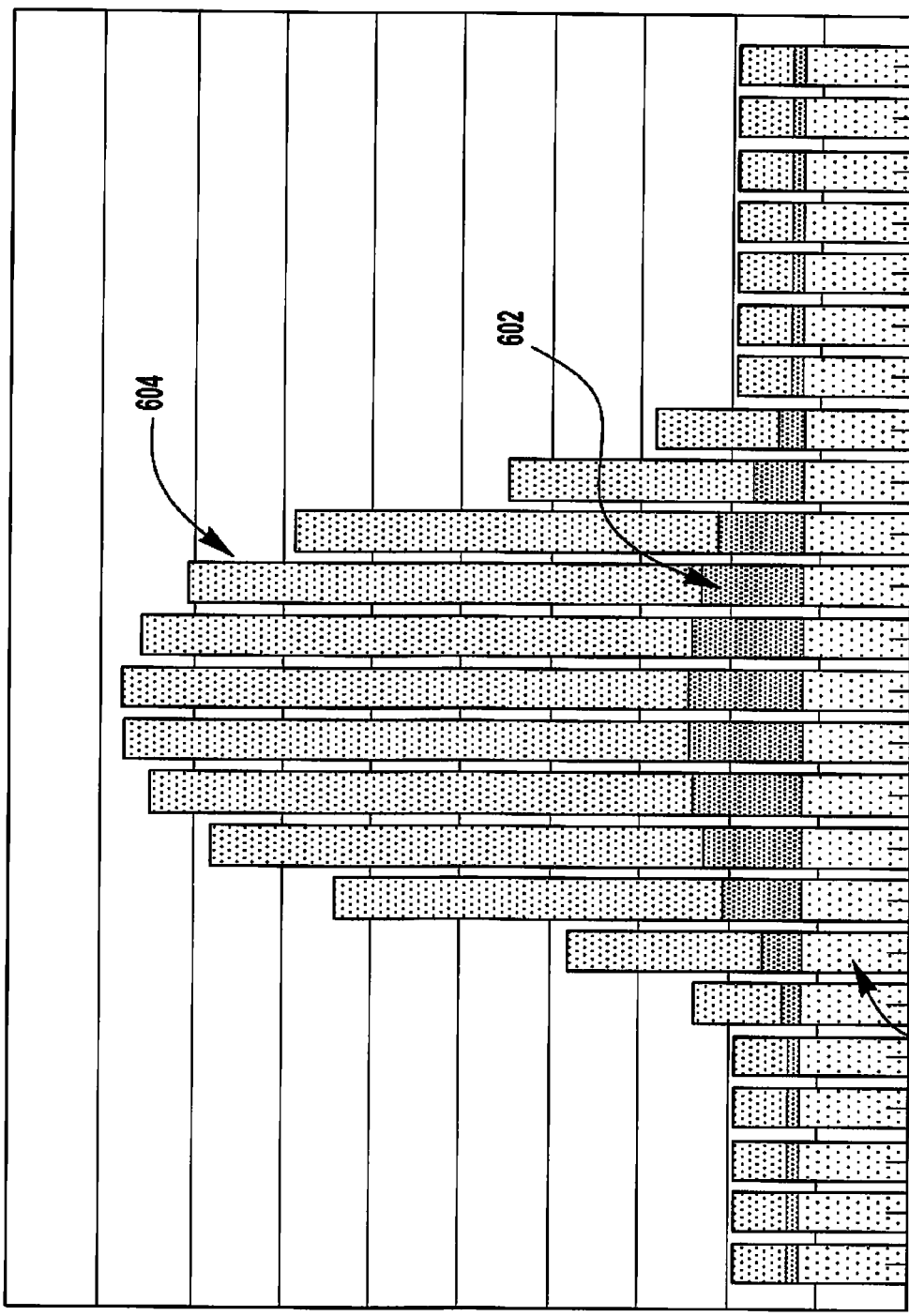
FIG. 6 is a graph illustrating the pattern of electricity demand over a 24-hour period, beginning at midnight and ending at midnight, in accordance with the present invention and the period during the day when demand could be supplied from an adjacent photoelectric field.

FIG. 6 illustrates a typical pattern of electricity demand over a 24-hour period, beginning at midnight and ending at midnight. Three types of demand make up the total demand. FIG. 6 illustrates the demand pattern as a bar chart.

Location 600 illustrates the demand for supporting internal illumination in the tubes 116 (FIG. 2) of the photobioreactor arrays 102 (FIG. 1). The demand is shown as constant throughout the 24-hour period, but it may vary by eliminating internal illumination during part of the daylight hours where there is no possibility of stopping the chemical reactions in the photosynthesis process.

Location 602 illustrates the parasitic demand generated by the consumption of pump drives, instrumentation, lighting, and other small consumers in the algae cultivation and processing and other components illustrated in FIG. 1. The consumption of the compressor drives is excluded. This demand generally will be constant during the nighttime hours and variable as illustrated in FIG. 6 during the daylight hours between about 6 am and 5 pm.

Location 604 illustrates the demand generated by the compressors incorporated in the processing scheme for the separation of carbon dioxide from oxygen, the liquefaction of oxygen, and the liquefaction of carbon dioxide, as is discussed by the descriptions herein before. This demand is essentially constant during the nighttime hours between about 6 pm and 5 am, but rises dramatically to a peak around noon during the daylight hours.

Electricity to meet a demand pattern such as is shown in FIG. 6 can be supplied in a variety of means. If it is entirely purchased, the cost would be based as a total of the energy consumed and the maximum demand during the billing cycle. Alternatively the electricity requirement could be self-generated. In general, base load electricity may be supplied by processing the oil free algae biomass by anaerobic digestion and employing off gases produced by the anaerobic digestion as fuel for the generation of electricity in a conventional generation installation. Another alternative is an installation of adjacent photovoltaic power generation, which having the same insolation pattern can supply the demand illustrated by 604.

Figure 7:
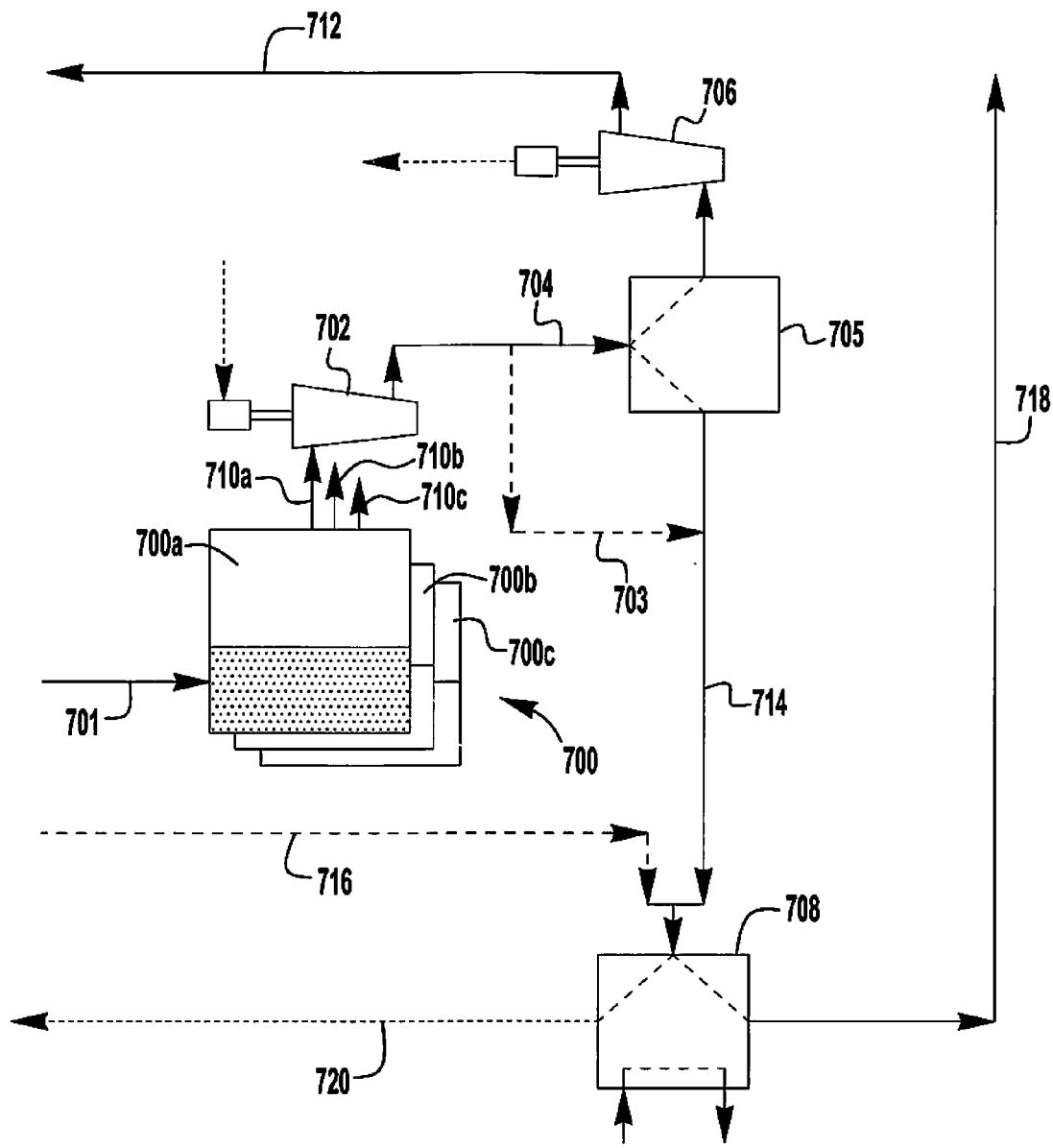
FIG. 7 illustrates a system for self-generating the portion of the electricity demand during the illustrative 24-hour period, which is essentially constant and does not necessarily include the peak demand, in accordance with the present invention.

FIG. 7 illustrates a method for self-generating the portion of the electricity demand during an illustrative 24-hour period, which is constant and need not include the peak demand. The source of the fuel for self-generation of the electricity is the essentially oil-free algae biomass residue.

Oil-free algae biomass 701 is fed to an anaerobic digester 700 in which, during an appropriate period of residence, is decomposed by bacterial action almost entirely to off gases containing a mixture of carbon dioxide and methane in about equal volumetric proportions. The digester 700 operates at some elevated pressure. Multiple digesters, such as for example digesters 700a, 700b, 700c, may be used depending on the quantity of biomass to be digested and the residence time required to complete the digestion.

The off gases from digestion are directed as streams 710a, 710b, 710c are compressed in compressor 702 to a pressure about the level that will ultimately be required for the generation of electricity. Two options then exist for the utilization of the off gases. One, Mode 703, the offgases are used as is for power generation. The other Mode 704, the components of the offgases are separated in the separation unit 705 as practically 100% carbon dioxide and practically 100% methane.

In Mode 704, the pressure of the separated carbon dioxide is reduced in expander 706 and delivered as a feed stream 712 to the photobioreactors 102 (FIG. 1). Some of the electricity supply is generated in the carbon dioxide expander 706 to compensate for the electricity consumed in the compressor 702.

For either mode 703 or 704, the gases from the compressor 702 become a fuel stream 714 for conventional combined-cycle power generation 708. Depending on the availability of algae biomass residue and the requirement for electricity, the fuel stream 714 for electricity generation can be supplemented by diverting some of the production of algae oil as a stream 716. The carbon content of the fuel is reflected in emissions of carbon dioxide to the atmosphere. The electrical output 720 of the conventional combined-cycle power generation 708 then supports the constant demand 600 illustrated in FIG. 6. Chimney gases exit combined-cycle power generation 708 through line 718.

For the peak demand 604 illustrated in FIG. 6, a supply of electricity is produced by the installation of a photovoltaic electricity generation field 730, as shown in FIG. 1, located adjacent to the field occupied by the photobioreactors 102. The photovoltaic field is equipped with inversion equipment 732 to produce alternating current. Since the peak occurs during the same hours of the day during which the photovoltaic field generates a peak output, the photovoltaic field operates essentially in synchronism with the demand for its output.

The method 100 of FIG. 1 requires two types of water supplies. One type is process water to supply the needs of the photosynthesis process. The other is cooled water for use in cooling in the heat exchangers 408, 420, 446, 490, and 512 illustrated in FIGS. 4 and 5. Cooled water is also required for condensing exhaust steam in combined-cycle power generation (FIG. 7), if this component is incorporated in the method illustrated in FIG. 1.

Figure 8:
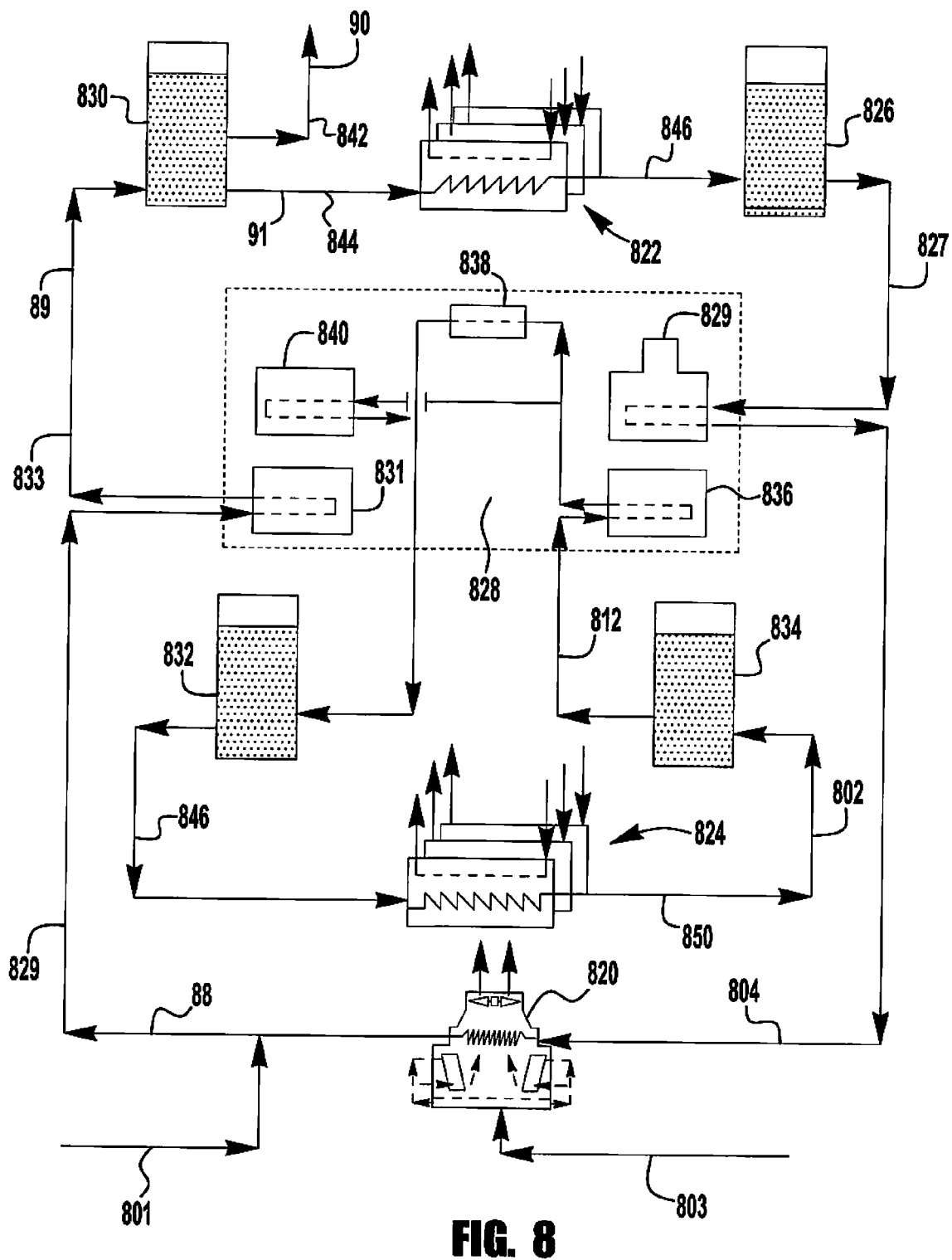
FIG. 8 illustrates a system for supplying the process water and for minimizing the consumption of makeup water in the supply of cooling water, in accordance with the present invention.

FIG. 8 illustrates a means for supplying the process water and for minimizing, if not eliminating, the need for makeup water for the supply of cooled water. The principles employed are the incorporation illustratively of an ammonia-based absorption-refrigeration component 828 and a wet and dry cooling tower component 820. The absorption refrigeration component 828 is conventional and comprises a generator 829, which receives its energy input through cooling the water stream 827 to stream 804, the evaporator 831, which provides the cooling for the entering stream 88 in line 829 and the leaving stream 89 in line 833. The remaining supporting equipment items in the refrigeration component 828 are the rectifier 838, the absorber 836, and the condenser 840.

The wet and dry cooling tower 820 operates in either the wet, dry, or combined modes to cool incoming heated water in stream 804 to the cooled water which with the addition of the process water requirement as stream 801 exits as stream 88 in line 829. Water that is evaporated in the wet mode is replaced by makeup water 803.

The need for wet cooling depends on the differences in atmospheric temperature between day and nighttime hours, which can be significant in desert or arid regions. To minimize the need for wet cooling, cooled water is stored in quantity in insulated storage tank 830.

The heat exchangers 822 are the combination of the individual heat exchangers 408, 420, 446, 490, and 512 as already noted, in which cooled water from storage tank entering as stream 91 in line 844 is heated to the stream in line 846 and storage in the heated-water storage tank 826. The heat exchangers 824 are the combination of the individual exchangers 474, 484, and 528 illustrated in FIGS. 4 and 5, in which incoming water in line 846 from heated water in storage tank 832 is cooled as stream 850 and delivered as stream 850 through line 802 to cold water storage tank 834. The absorption refrigeration component operates by receiving cold water from storage tank 834 through line 812 and used to provide the cooling effect in the absorber 836. The water thus heated in returned to the heated water storage 832, and is thereby recycled.

The heated water in storage tank 826 is cooled in sequential steps. In Step (1), it is delivered through line 827 to the generator 829 in the absorption refrigeration component, where it is cooled. In Step (2) it is then delivered through line 804 to the wet and dry cooling tower, where it is further cooled. In Step (3) it is delivered with the process makeup water (Stream 801) as stream 88 through line 829 to the evaporator 831, where it is finally cooled. This cooled water is delivered to the storage tank 830 as stream 89 in line 833. The process makeup water is taken from storage tank 830 as stream 90 through line 842.

The operation of the cooled-water supply follows a pattern of variation, which depends on the pattern of insolation and the pattern of variation in atmospheric air temperatures and humidities, both during a 24-hour day. The consumption of makeup water depends on these patterns.

OTHER EMBODIMENTS

The description of the features of the preferred embodiments has focused on the installation covered by the invention being capable for receiving a fixed quantity of essentially pure carbon dioxide continuously during the day and throughout the year, despite the fact that the installation is only fully operable during most of the daylight hours. Nevertheless, it should be fully understood that the installation covered by this invention can accept carbon dioxide at variable rates up to its capacity. Variations in rate of receipt will affect only the operating conditions, which should then be adjusted. The inventory of equipment items comprising the installation would remain unaffected.

The method may operate in an alternative mode than receipt of carbon dioxide on a 24/7 basis. The method may receive carbon dioxide at variable rates that do not exceed the design capacities of the component equipment, for processing and storage, which are set for a fixed 24/7 receipt rate.

In FIG. 1, the system 100 may embody a separation of the functions of the $CO_2/O_2$ separation and oxygen liquefaction system 124. A separation component may be embodied in which the carbon dioxide is separated from the oxygen in the off gases from the photobioreactors 102 as a liquid and delivered to the carbon dioxide storage container 526 (See FIG. 5). Another separation component may be embodied to accept the separated oxygen vapor in which the appropriate proportion of the oxygen is then liquefied. The refrigerant loop of streams 72 and 87 is then divided appropriately as required by the embodiment of the separated components.

The separated component in which the carbon dioxide is separated from oxygen may embody alternative separation methods through, as examples, the employment of conventional amine absorption/liberation technology or the ammonium carbonate/bicarbonate cycle. In either case, provision is incorporated for interim storage for the rich and lean solutions to accommodate variations in throughputs and demands during a typical day.

In FIGS. 2 and 3, the system 100 may embody the removal of the parabolic reflectors 110a-110i with closer spacing of the photobioreactor tubes 104 either as a single layer or as a double layer with triangular pitch to connect the ends of the tubes. Periodically, the spacing between the photobioreactor tubes 104 may be increased to allow for the installation of cooling heat exchangers 214 and of mixing devices 216, as shown in FIG. 3.

In FIG. 4, the system 100 may embody the substitution of either or both of the expansion valves 460 and 498 with turbo expanders, which produce the same processing effect of pressure reduction but with simultaneous generation of by-product electricity. This embodiment depends on tradeoff between increased capital cost and reduced operating cost compared to the use of expansion valves.

In FIG. 4, the system may embody the substitution of the internally supplied refrigeration 202 and 204 by externally supplied refrigeration employing any commercial refrigerant such as R134a or ammonia.

In FIG. 4 the system may embody alternative configurations of the coolers as may be found appropriate for the goal of achieving minimized enthalpy of the fluid stream 60 before expansion. Likewise, the system may embody alternative pressure levels in the flowing fluids as may be found appropriate to reducing the energy required for compression throughout the Method. The system may embody the use of steam turbine driven prime movers to operate compressors 404, 416, 442, and 488 as an alternative to electrically-driven motors.

In FIG. 5 the method may embody the use of storage of elevated-pressure carbon dioxide in underground caverns or formations, which are geologically suitably sealed to avoid leakage of stored carbon dioxide and which are located in the vicinity of the photobioreactor installations. The use of the condensation equipment and the associated compression equipment is thereby replaced by compression and expansion equipment for storing and recovering carbon dioxide as required by insolation in the photobioreactors.

In FIG. 5 also the Method may embody the use of storage of solid carbon dioxide (dry ice) in suitable insulated containers. Operating conditions may be changed as required and equipment provided for producing dry ice from excess carbon dioxide not needed in the photobioreactors, transporting the dry ice to and from storage, heat exchange equipment for the evaporation of dry ice when needed by the photobioreactors.

FIG. 6 illustrates the variation in electricity demand through a typical day. Similar variations also occur in the heat exchange duties in the coolers. The system may embody parallel equipment units for the compressors and heat exchangers of varied capacity ranges, each unit operable at predetermined times throughout a typical day to enable the system to operate effectively and efficiently.

In FIG. 5 the system may embody the substitution of the expansion valve 518 with a turbo expander, which produces the same processing effect of pressure reduction but with simultaneous generation of by-product electricity. This embodiment depends on tradeoff between increased capital cost and reduced operating cost compared to the use of expansion valves.

In FIG. 5, the system may embody the elimination of streams 72 and 87 in the event that the internal refrigeration requirement in FIG. 4 is substituted by refrigeration from an external source.

In FIG. 5, the system may embody alternative configurations of the coolers as may be found appropriate, for example, if external refrigeration is employed, for the goal of achieving minimized enthalpy of the fluid of stream 81 before expansion. Likewise, the system may embody alternative pressure levels in the flowing fluids as may be found appropriate to reducing the energy required for compression throughout the system. The system may embody the use of steam-turbine driven prime movers to operate the compressors as an alternative to electrically-driven motors.

In FIG. 6, the system may embody a supply of electricity during peak demand hours through solar generation through conventional steam generation and turbo expansion cycles.

In FIG. 7, the system may embody the elimination of the off gases separation unit 705 and the combined-cycle power generation unit 708 in the event the source of carbon dioxide is an adjacent coal gasification installation in which such a separation unit is normally incorporated. The carbon dioxide thus separated can be returned for processing as in FIG. 1 and the methane used externally as additional fuel to help provide the Method's needs for electricity.

In FIG. 8 the system, depending on operating and environmental conditions, may embody alternative modes of absorption refrigeration such as the use of lithium bromide solutions in which the refrigerant is water.

In FIG. 4, if the immediate vicinity of the location of an installation employing the present invention is geologically suited for underground storage of carbon dioxide under pressure, the liquid carbon dioxide 428 may be stored underground instead of in insulated surface tanks and subsequently released as required.

In FIG. 5, also if the immediate vicinity of the location of an installation employing the present invention is geologically suited for underground storage of carbon dioxide under pressure, liquefaction of the carbon dioxide nighttime input 70 may be avoided and instead the input carbon dioxide gas stream sent as a stream compressed for underground storage and retrieval.

In FIG. 4, if marketing conditions permit and the oxygen by-product can be delivered at the variable rates of production instead of at a specified fixed rate, the installation of the liquefaction and storage equipment can be avoided and, instead, the oxygen exported at required pressure at the variable production rates.

For all of the embodiments described herein variations in the distance between the algae cultivation and processing system and any of the three modes of fossil energy production systems can exist. Accordingly, the embodiments embody linkages over variable distances of separation such that interchanges continue as linkages as described in this invention through transportation in pipelines and/or railway or highway tank cars or vehicles.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above described components (assemblies, devices, etc.) the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

The invention claimed is:

1. A method for cultivating and processing microalgae, comprising:
   directing a continuous supply of carbon dioxide into an enclosed photobioreactor containing microalgae;
   exposing the enclosed photobioreactor to insolation for the cultivation of the microalgae by means of controlled photosynthesis chemical reactions;
   cultivating the microalgae and processing the microalgae to create an algae biomass and a gaseous mixture;
   separating the algae biomass from the gaseous mixture;
   extracting and separating the algae biomass as essentially pure algae oil and oil-free algae biomass;
   separating the gaseous mixture into unreacted carbon dioxide for recycling and oxygen for export;
   recycling the separated unreacted carbon dioxide to the photobioreactor;
   storing the oxygen in preparation for export;
   wherein the separation of the gaseous mixture into unreacted carbon dioxide and oxygen comprises:
   compressing the gaseous mixture of unreacted carbon dioxide and oxygen;
   cooling the compressed gaseous mixture to a temperature where the carbon dioxide condenses into a liquid carbon dioxide and can be separated from the oxygen;
   reducing the pressure of the liquid carbon dioxide to a level required for storage;
   separating the carbon dioxide thus produced as vapor, and recycling the carbon dioxide vapor for recompression and condensation; and
   compressing the oxygen separated from the liquid carbon dioxide to pressure levels causing a liquefaction of the oxygen.

2. The method of claim 1 including:
   delivering the separated unreacted carbon dioxide to the photobioreactor at rates suited to the pattern of insolation during the 24-hour day;
   storing excess unreacted carbon dioxide from the photobioreactor as a liquid; and
   releasing through evaporation stored unreacted carbon dioxide to the photobioreactor when the photobioreactor demand exceeds the delivery of unreacted carbon dioxide.

3. The method of claim 2 including directing the unreacted carbon dioxide stored as a liquid through an evaporator and then as a vapor to the photobioreactor.

4. The method of claim 3 including directing process water and nutrients into the photobioreactor.

5. The method of claim 4 including:
flowing reactants including carbon dioxide, water and nutrients at predetermined rates through photobioreactor tubes containing microalgae;
maintaining a level of photosynthesis within the photobioreactor tube during periods when insolation is lacking.

6. The method of claim 5 further including:
configuring the photobioreactor tubes by a plurality of interconnected circular tubes, disposed in parallel flow paths, each path having a length for flow established to produce algae at a desired production level.

7. The method of claim 6 further including:
providing a plurality of reflecting parabolic insolation accumulators each having a reflecting parabolic surface;
disposing the plurality of reflecting parabolic insolation accumulators so that a center of each of the circular interconnected tubes is located coincident with a focal point of its reflecting parabolic surface such that insolation received by an area of the reflecting surface is concentrated on the circular interconnected tubes to a degree.

8. The method of claim 7 including:
orienting the circular interconnected tubes in a north-south direction; and
rotating the parabolic reflectors about a vertical axis in synchronization with the movement of the sun in the sky from dawn until sunset.

9. The method of claim 7 including concentrating wavelengths of internal illumination within the circular interconnected tubes in low ends and high ends of visible spectrum which are optimum for enhancing algae cultivation.

10. The method of claim 7 including cooling the reactants in heat exchangers located between adjacent circular interconnected tubes, within which algae cultivation occurs, to maintain a temperature range.

11. The method of claim 10 including providing mixing devices located between circular interconnected tubes to direct portions of the reactants toward an inside surface of the interconnected tubes, which portions have not received insolation because of inability of photons of the insolation to penetrate to an interior of the interconnected tubes.

12. The method of claim 1 wherein the separation of the gaseous mixture into unreacted carbon dioxide and oxygen comprises:
compressing the gaseous mixture of unreacted carbon dioxide and oxygen;
cooling the compressed gaseous mixture to a temperature where the carbon dioxide condenses into a liquid carbon dioxide and can be separated from the oxygen; and
storing the carbon dioxide liquid in one or more suitable underground geological formations.

13. The method of claim 1 including dividing the oxygen separated from the liquid carbon dioxide into a first portion subjected to reduction in pressure to a level required for marketing and into a second portion subjected to liquefaction and storage.

14. The method of claim 1 including delivering the oxygen separated from the liquid carbon dioxide under pressure at variable rates of production.

15. The method of claim 1 wherein compressing oxygen vapor from the gaseous mixture to pressure levels causing the liquefaction of the oxygen, comprises:
cooling the oxygen vapor;
refrigerating the cooled oxygen vapor by evaporating liquid carbon dioxide; and
reducing the oxygen vapor pressure by passing the cooled oxygen vapor through an expansion valve whereby the liquefaction of oxygen occurs.

16. The method of claim 1 wherein compressing the oxygen vapor from the gaseous mixture to pressure levels causing the liquefaction of the oxygen, comprises:
cooling the oxygen vapor;
refrigerating the cooled oxygen vapor by evaporating liquid carbon dioxide; and
reducing the pressure of the oxygen vapor by passing the cooled oxygen vapor through an expansion turbine with a production of by-product electricity.

17. The method of claim 1 wherein compressing the oxygen vapor from the gaseous mixture to pressure levels causing the liquefaction of the oxygen, comprises:
cooling the oxygen vapor;
refrigerating the cooled oxygen vapor with external sources employing a commercial refrigerant; and
reducing the oxygen vapor pressure by passing the cooled oxygen vapor through an expansion valve whereby the liquefaction of oxygen occurs.

18. The method of claim 1 wherein the liquefaction of carbon dioxide vapor from the gaseous mixture includes:
compressing the carbon dioxide vapor; and
cooling the compressed carbon dioxide to generate liquefied carbon dioxide.

19. The method of claim 18 including:
reducing the pressure of the liquefied carbon dioxide to a level required for storage in a flash drum as carbon dioxide vapor; and
recycling associated carbon dioxide vapor for recompression.

20. The method of claim 1 including:
reducing the pressure of the liquefied carbon dioxide by passing the liquefied carbon dioxide through passage in an expansion turbine; and
generating electricity by passing the liquefied carbon dioxide through passage in an expansion turbine.

21. The method of claim 1 wherein requirements for electricity are provided by:
providing a photovoltaic field adjacent to the photobioreactor; and
producing alternating current electricity with inversion equipment to match a frequency and voltage of electricity otherwise supplied.

22. The method of claim 1 including:
supplying base load electricity by processing the oil-free algae biomass by anaerobic digestion and employing off gases produced by the anaerobic digestion as fuel for generation of electricity in a conventional generation installation.

23. The method of claim 22 including:
separating carbon dioxide from methane in the off gases from anaerobic digestion;
using the methane as fuel for electricity generation; and
replacing a portion of incoming unreacted carbon dioxide to the photobioreactor with the carbon dioxide in the off gases from anaerobic digestion.

24. The method of claim 23 including:
exporting the off gases to an adjacent fossil-energy installation;
separating the carbon dioxide and methane in the off gases in the adjacent fossil-energy installation;
combining the carbon dioxide with the incoming unreacted carbon dioxide produced in the adjacent fossil-energy installation to the photobioreactor;

supplementing fuel in the adjacent fossil-energy installation with the methane extracted from the off gases; and including incremental electricity generated in the fossil-energy installation that is exported for use in cultivating and processing microalgae.

25. The method of claim 4 including supplying the process water by:

storing heated water and cooled water within a hot water storage container and a cold water storage container, respectively;

cooling the heated water with absorption refrigeration having an appropriate medium as a refrigerant; and cooling the heated water with a combined induced-draft wet and a dry cooling tower.

26. The method of claim 25 including:

supplying heated water from the hot water storage container at an elevated temperature input required by absorption refrigeration;

supplying cold water from the cold water storage container for at a low temperature input required for cooling streams leaving compressors; and supplying heated water from the hot water storage container for evaporation of liquefied oxygen and liquefied carbon dioxide.

27. The method of claim 25 including:

combining the process water with circulating water to provide a makeup water of reduced temperature for the photobioreactor.

28. The method of claim 4 including supplying the process water by:

storing heated water and cooled water within a hot water storage container and a cold water storage container, respectively;

cooling the heated water with lithium bromide having water as a refrigerant in an absorption refrigeration component; and cooling the heated water with an induced-draft, combined dry-and-wet cooling tower.

* * * * *